United States Patent
Kikuchi et al.

(10) Patent No.: US 12,337,045 B2
(45) Date of Patent: *Jun. 24, 2025

(54) LIQUID COSMETIC

(71) Applicant: L V M H Recherche, Saint Jean de Braye (FR)

(72) Inventors: Masahiro Kikuchi, Tokyo (JP); Mai Ozawa, Tokyo (JP); Takayoshi Sakoda, Tokyo (JP)

(73) Assignee: L V M H Recherche, Saint Jean de Braye (FR)

( * ) Notice: Subject to any disclaimer, the term of this patent is extended or adjusted under 35 U.S.C. 154(b) by 636 days.

This patent is subject to a terminal disclaimer.

(21) Appl. No.: 17/415,693

(22) PCT Filed: Dec. 19, 2018

(86) PCT No.: PCT/IB2018/001601
§ 371 (c)(1),
(2) Date: Jun. 17, 2021

(87) PCT Pub. No.: WO2020/128559
PCT Pub. Date: Jun. 25, 2020

(65) Prior Publication Data
US 2022/0040063 A1    Feb. 10, 2022

(51) Int. Cl.
| | | |
|---|---|---|
| *A61K 8/11* | (2006.01) | |
| *A61K 8/73* | (2006.01) | |
| *A61K 8/81* | (2006.01) | |
| *A61Q 19/00* | (2006.01) | |

(52) U.S. Cl.
CPC ............... *A61K 8/11* (2013.01); *A61K 8/73* (2013.01); *A61K 8/8147* (2013.01); *A61Q 19/00* (2013.01); *A61K 2800/48* (2013.01); *A61K 2800/56* (2013.01)

(58) Field of Classification Search
CPC .......... A61K 8/11; A61K 8/73; A61K 8/8147; A61K 2800/48; A61K 2800/56; A61K 8/04; A61K 8/34; A61K 8/8152; A61Q 19/00; A61Q 1/00

USPC ......................................................... 424/401
See application file for complete search history.

(56) References Cited

U.S. PATENT DOCUMENTS

| | | |
|---|---|---|
| 6,818,296 B1 | 11/2004 | Garces Garces et al. |
| 11,478,410 B2 * | 10/2022 | Kikuchi ............ A61Q 19/00 |
| 2008/0233057 A1 * | 9/2008 | Viladot Petit ....... A61Q 11/00 424/49 |
| 2013/0164242 A1 * | 6/2013 | Tamareselvy .......... A61Q 5/06 424/78.02 |

FOREIGN PATENT DOCUMENTS

| | | |
|---|---|---|
| EP | 1064911 A1 | 1/2001 |
| EP | 1972361 A1 | 9/2008 |
| JP | 2000302662 A | 10/2000 |
| JP | 2003238351 A * | 8/2003 |
| JP | 2005-179290 A | 7/2005 |
| WO | WO 2007/068391 | 6/2007 |

OTHER PUBLICATIONS

"Kobayashi, JP-2003238351-A, Aug. 27, 2003, Machine translation" (Year: 2003).*
ICI Americas Inc, The HLB system—a time saving guide to emulsifier selection. Chemmunique (Ed.), (1980). . Delaware, USA (Year: 1980).*
Japanese Office Action issued in corresponding Japanese Patent Application No. 2021-535087 (issued on Jan. 10, 2023).
International Search Report in International Application No. PCT/IB2018/001601 (issued on Jul. 31, 2019).

* cited by examiner

*Primary Examiner* — Isaac Shomer
*Assistant Examiner* — Bryan James Rego
(74) *Attorney, Agent, or Firm* — Panitch Schwarze Belisario & Nadel LLP; Erin M. Dunston; Christopher L. North

(57) ABSTRACT

The invention provides a liquid cosmetic that contains at least a capsule in an aqueous phase, wherein the capsule comprises agar shell encapsulating an oil component, and the aqueous phase comprises one thickener selected from the group consisting of a (meth)acrylic polymer and a polysaccharide, and an amphiphilic substance having an HLB value of no greater than 13.

12 Claims, No Drawings

LIQUID COSMETIC

CROSS-REFERENCE TO RELATED APPLICATIONS

This application is a U.S. National Stage Application pursuant to 35 U.S.C. § 371 of International Patent Application PCT/IB2018/001601, filed on Dec. 19, 2018, and published as WO 2020/128559 on Jun. 25, 2020, all of which are incorporated herein by reference in their entireties for all purposes.

TECHNICAL FIELD

The present invention relates to a liquid cosmetic.

BACKGROUND ART

Cosmetics in the form of cosmetic lotion, emulsion or essences have traditionally been used to help moisturize the skin and remedy problems such as roughened skin. Some recent types of cosmetic materials include dispersed capsules containing gel particles or beautifying ingredients. Japanese Unexamined Patent Publication No. 2000-302662 discloses a capsule-containing gelated cosmetic having a cosmetic component encapsulated or impregnated in capsules formed of agar and a polyvalent metal salt of alginic acid, with the capsules dispersed in a water-soluble gel.

But when such a conventional cosmetic having capsules dispersed in an aqueous phase is prepared, it usually becomes turbid over time, which not only adversely affects the appearance of the cosmetic but also impairs its homogeneity, and when it is subsequently applied to the skin it fails to adequately exhibit its original moisturizing or emollient effect.

The Applicant has found that when capsules are added to a liquid aqueous phase, the capsules tend to suffer damage by the effects of impact and time-dependent change. Consequently, outer shells of the damaged capsules and the contents that have leaked out of the capsules tend to produce turbidity in the aqueous.

So it is an object of the present invention to provide a liquid cosmetic comprising capsules in an aqueous phase (a capsule-containing liquid cosmetic), which has less turbidity produced over time while maintaining its original cosmetic effect over extended periods.

SUMMARY OF THE INVENTION

Specifically, the invention provides a liquid cosmetic containing at least a capsule in an aqueous phase, wherein the capsule comprises agar shell encapsulating an oil component, and the aqueous phase comprises one thickener selected from the group consisting of a (meth)acrylic polymer and a polysaccharide, and an amphiphilic substance having an HLB value of no greater than 13.

The Applicant has found that such liquid cosmetic according to the invention exhibits less turbidity over time while maintaining its original cosmetic effect over extended periods.

In fact, with the liquid cosmetic of the invention, however, since an agar shell are used as a capsule, and one thickener selected from the group consisting of a (meth)acrylic polymer and a polysaccharide and an amphiphilic substance having an HLB value of no greater than 13 are added to an aqueous phase, it is possible to minimize damage caused by impact between the capsules or leakage of the capsule contents, and to reduce turbidity of the aqueous phase. Moreover, since the liquid cosmetic of the invention maintains high stability over time, its original effect is maintained over long periods.

The liquid cosmetic includes agar in the capsule outer shell, and the moisture-retaining property of the agar itself increases the effect of moisture retention on the skin, tending to provide more continuous moisture retention. Moreover, the oil component encapsulated in the capsule(s) can provide a moisturizing, nourishing and emollient effect on the skin.

The amphiphilic substance itself also has a moisture-retaining property for skin. The liquid cosmetic can therefore further increase the effect of retaining moisture on skin.

The aqueous phase may additionally include a perfume. When adding a perfume to an aqueous phase of a liquid cosmetic it is often necessary to add a solubilizer to solubilize the perfume. However, since a solubilizer promotes damage to the capsules, addition of a solubilizer to the aqueous phase with further addition of a perfume has been difficult for capsule-containing liquid cosmetics. In the liquid cosmetic of the invention, however, the specific amphiphilic substance can both prevent damage to the capsules and solubilize the perfume. Damage to the capsules can therefore be minimized even when a perfume is added to the aqueous phase. Moreover, addition of a perfume to the aqueous phase allows the resulting cosmetic to have an excellent fragrance even with addition in a minimal amount.

The aqueous phase may also contain a low molecular polyol. The aqueous phase may contain an aryloxyalkanol.

The capsules may be present in a dispersed state in the aqueous phase. The liquid cosmetic described above can be used with the capsule and aqueous phase in a well-balanced combination, allowing the function of the cosmetic to be easily and reliably exhibited. The appearance of the liquid cosmetic also has an excellent aesthetic quality.

The present invention also relates to a cosmetic process for caring for and/or making-up keratinic materials, in particular providing a moisturizing, nourishing and emollient effect, comprising the application onto keratinic materials, in particular onto skin, of the liquid cosmetic as defined in the invention.

By 'keratinic materials', it means skin and/or lips, preferably skin.

DETAILED DESCRIPTION OF THE INVENTION

Embodiments of the invention will now be described. However, the present invention is not limited to the embodiments described below.

The abbreviation "POE" used herein stands for polyoxyethylene. The abbreviation "PEG" stands for polyethylene glycol.

The liquid cosmetic (capsule-containing liquid cosmetic) according to a preferred embodiment comprises a least a capsule with oil component-encapsulating agar shell in an aqueous phase.

Capsules with Oil Component-Encapsulating Agar Shell

Here, "a capsule" means a particle composed of agar shells and their contents, the contents being encapsulated in the outer shell. The capsule shapes may be spherical or spindle-shaped, for example.

The term "agar shell" refers to an outer shell containing agar, and it may consist entirely of agar or may alternatively contain components other than agar. Such other components other than agar may be alginic acid salts, carrageenan and the like, which include alginic acid salts including inorganic salts such as sodium salts, potassium salts, ammonium salts and lithium salts. Because agar easily retains moisture, the presence of agar in the capsule outer shells increases the moisturizing effect of the liquid cosmetic on skin while also lengthening the duration of the moisturizing effect. In order to improve its durability of the outer shell, it is preferred for the outer shells to consist entirely of agar.

The oil component contained in the capsule comprises (1) an oil, (2) an oil soluble or dispersible component or (3) a combination thereof. So long as it comprises components (1) to (3), the oil component may also contain other components in amounts such that the effect of the invention is not impeded.

Oils include hydrocarbon oils, fat oils, waxes, hydrogenated oils, ester oils, fatty acids, silicone oils, fluorine-based oils, and mixtures thereof. By encapsulating an oil component in the capsules, the liquid cosmetic is able to provide a high nourishing effect for skin.

Hydrocarbon oils include liquid paraffin, light liquid isoparaffin, dodecane, isododecane, tetradecane, isotetradecane, hexadecane, isohexadecane, squalane, vegetable squalane, vaseline, polyisobutylene, polybutene, other oils, and mixtures thereof.

Fat oils include Japan wax, olive oil, castor oil, mink oil, macadamia nut oil, camellia oil, rose hip oil and avocado oil.

Waxes include beeswax, lanolin, carnauba wax, candelilla wax, spermaceti wax and mixtures thereof.

Ester oils include jojoba oil, cetyl isooctanoate, glyceryl tri(caprylate/caprate), isopropyl myristate, isopropyl palmitate, octyldodecyl myristate, glyceryl trioctanoate (triethylhexanoin), polyglyceryl diisostearate, diglyceryl triisostearate, glyceryl tribehenate, diisostearyl malate, neopentylglycol dioctanoate, cholesterol fatty acid esters and mixtures thereof.

Fatty acids include lauric acid, myristic acid, palmitic acid, stearic acid, behenic acid, oleic acid, other fatty acids and mixtures thereof.

Silicone oils include polydimethylsiloxane (dimethicone), polymethylphenylsiloxane (diphenyldimethicone), phenyltrimethicone, diphenylsiloxyphenyltrimethicone, amino-modified silicone, epoxy-modified silicone, carboxy-modified silicone, polyether-modified silicone, alkyl-modified silicone, fluorine-modified silicone and mixtures thereof.

Fluorine-based oils include perfluoropolyethers, perfluorodecalin, perfluorooctane and mixtures thereof.

Examples for the oil soluble or dispersible component include colorants, active ingredients and mixtures thereof.

The oil(s) content may be from 0 to 100 mass %, but is preferably from 50 to 100 mass %, based on the total mass of the oil component (the capsule contents). If the oil content is 0 mass %, the oil soluble or dispersible component will constitute the total mass.

Colorants that may be added to the oil component include oil-soluble colorants, oil-dispersible colorants and mixtures thereof. Oil-soluble colorants may be types that dissolve only in oils, or that dissolve in both oils and alcohols. Marigold colorant is an example of a colorant that dissolves only in oils. Blue #403 (Sudan Blue B) is an example of a colorant that dissolves in both oils and alcohols. An oil-dispersible colorant need only be a colorant that is dispersible in oils, and it may be one that is classified as a water-soluble colorant. Examples of oil-dispersible colorants include Red #104-(1), Yellow #4, Blue #1 and Violet #201.

The colorant(s) content may be 0 to 20 mass %, for example, based on the total weight of the oil component (the capsule contents).

Active ingredients that may be added to the oil component may be components that have beautifying effects on the skin, including effects against skin roughening and wrinkles, for example. Examples of such active ingredients include fat-soluble vitamins, and specifically vitamin A compounds such as retinol, retinol palmitate and retinol acetate, vitamin D compounds such as ergocalciferol and cholecalciferol, vitamin E compounds such as tocopherol and tocotrienol, and mixtures thereof. Active ingredients may also function as colorants, as is the case with carotenoids such as astaxanthin, lycopene fucoxanthin, and mixtures thereof.

The active ingredient(s) content may be from 0 to 100 mass %, based on the total mass of the oil component (the capsule contents), and is preferably from 0 to 50 mass % based on the total mass of the oil component (the capsule contents).

The capsules have a mean particle size of preferably 0.1 mm or greater, more preferably 0.3 mm or greater and even more preferably 0.5 mm or greater, and preferably no greater than 8 mm, more preferably no greater than 6 mm and even more preferably no greater than 4 mm. In other words, the capsules have a mean particle size from 0.1 mm to 8 mm, in particular from 0.3 mm to 6 mm, more preferably from 0.5 mm to 4 mm. This will ensure that the shell thickness is sufficient to allow the oil component to be completely encapsulated, while providing the capsules with an excellent appearance. The mean particle size of the capsules can be determined, for example, by photographing a region containing a minimum of 10 particles of the liquid cosmetic, and determining the average size from the image.

The thickness of the outer shells of the capsules is preferably from 2 to 90% of the mean particle size of the capsules, the percentage being more preferably from 5 to 80%. Restricting the outer shell thicknesses to within this range can more effectively prevent leakage of the oil component inside them and reduce damage by impact.

For an even higher moisturizing effect exhibited by the liquid cosmetic, the capsule(s) content is preferably 5 mass % or greater, more preferably 10 mass % or greater and even more preferably 15 mass % or greater, based on the total liquid cosmetic mass (weight). The capsule(s) content is also preferably no greater than 65 mass %, more preferably no greater than 60 mass % and even more preferably no greater than 55 mass % based on the total liquid cosmetic mass, in order to more effectively minimize disintegration of the capsule agar shells and to obtain a liquid cosmetic with an excellent appearance. In other words, the capsule(s) content may be from 5 to 65 mass %, from 5 to 60 mass %, from 5 to 55 mass %, from 10 to 65 mass %, from 10 to 60 mass %, from 10 to 55 mass %, from 15 to 65 mass %, from 15 to 60 mass % or preferably from 15 to 55 mass %, based on the total mass (weight) of the liquid cosmetic.

Thickener (Rheological Modifier)

The aqueous phase contains water, one thickener (rheology modifier) selected from the group consisting of a (meth)acrylic polymer and a polysaccharide, and an amphiphilic substance having an HLB value of no greater than 13. The term "(meth)acrylic" refers to acrylic or methacrylic, and the same applies to other similar structures.

The water used may be distilled water, purified water, hot spring water, deep water, or plant-derived steam distilled water such as lavender water, rose water or orange flower water. The water content may be a minimum of 10 mass %, 15 mass % or 20 mass %, to a maximum of 80 mass %, 75 mass % or 70 mass %, based on the based on the total mass (weight) of the liquid cosmetic. That is, the water content may be from 10 to 80 mass %, from 10 to 75 mass %, from 10 to 70 mass %, from 15 to 80 mass %, from 15 to 75 mass %, from 15 to 70 mass %, from 20 to 80 mass %, from 20 to 75 mass % or preferably from 20 to 70 mass %, based on the total mass (weight) of the liquid cosmetic.

(Meth)Acrylic Polymers

The (meth)acrylic polymer may be an alkyl (meth)acrylate copolymer, (meth)acrylic acid-alkyl (meth)acrylate copolymer or its salt, or a derivative or salt of a (meth) acrylic acid-alkyl (meth)acrylate copolymer and mixtures thereof. The copolymers mentioned above also include their crosslinked forms and mixtures thereof.

Some of the available copolymers include the alkyl acrylate copolymer: ACULYN 33 (Rohm & Haas); the acrylic acid-alkyl methacrylate copolymers (also crosslinked): PEMULEN TR-1, PEMULEN TR-2, CARBOPOL ETD2020, CARBOPOL 1382, CARBOPOL 1342, ULTREZ 20 polymer and ULTREZ 21 polymer (Lubrizol Advanced Materials); AQUPEC HV-501ER, AQUPEC SER W-300C and AQUPEC SER W-150C (Sumitomo Seika Chemicals Co., Ltd.); and (meth)acrylic acid-alkyl (meth) acrylate copolymer derivatives or their salts, such as polyoxyethylenealkyl ether ester copolymers of acrylic acid-methacrylic acid-alkyl acrylate-alkyl methacrylate-methacrylic acid, having a polyoxyethylenealkyl ether ester-bonded to a (meth)acrylic acid-alkyl (meth)acrylate copolymer (such as alkyl acrylate-alkyl methacrylate-polyoxyethylene(20) stearyl ether copolymer (ACULYN 22, Rohm & Haas)).

Preferred (meth)acrylic polymers are Acrylate/C10-30 Alkyl Acrylate and Acrylate/C10-30 Alkyl Acrylate Crosspolymer. Specifically, preferred copolymers are any one or more selected from among (a) copolymers wherein the monomer units are an alkyl (meth)acrylate ester containing an alkyl group of 10 to 30 carbon atoms, and (meth)acrylic acid, (b) crosslinked copolymers wherein the monomer units are an alkyl (meth)acrylate ester with an alkyl group of 10 to 30 carbon atoms, (meth)acrylic acid, and pentaerythritol allyl ether, (c) crosslinked copolymers wherein the monomer units are an alkyl (meth)acrylate ester containing an alkyl group of 10 to 30 carbon atoms, (meth) acrylic acid and sucrose allyl ether, and (d) crosslinked copolymers wherein the monomer units are an alkyl (meth) acrylate ester containing an alkyl group of 10 to 30 carbon atoms, (meth)acrylic acid, pentaerythritol allyl ether and sucrose allyl ether. PEMULEN TR-1, PEMULEN TR-2, CARBOPOL ETD2020, CARBOPOL 1342, CARBOPOL 1382, ULTREZ 20 polymer, ULTREZ 21 polymer, AQUPEC SER W-300C and AQUPEC SER W-150C mentioned above correspond to such copolymers.

The (meth)acrylic polymer content is preferably 0.01 mass % or greater, more preferably 0.05 mass % or greater and even more preferably 0.08 mass % or greater, and preferably no greater than 0.8 mass %, more preferably no greater than 0.5 mass % and even more preferably no greater than 0.3 mass %, based on the total mass of the liquid cosmetic. In other words, the (meth)acrylic polymer(s) content may be from 0.01 to 0.8 mass %, from 0.01 to 0.5 mass %, from 0.01 to 0.3 mass %, from 0.05 to 0.8 mass %, from 0.05 to 0.5 mass %, from 0.05 to 0.3 mass %, from 0.08 to 0.8 mass %, from 0.08 to 0.5 mass % or preferably from 0.08 to 0.3 mass %, based on the total mass of the liquid cosmetic. This can increase the viscosity of the aqueous phase and further reduce impact between the capsules. It can also minimize damage to the outer shells of the capsules, and further reduce production of turbidity with the passage of time.

Polysaccharides

The polysaccharide may be selected in the group consisting of xanthan gum, hyaluronic acid, sodium hyaluronate or acetylated hyaluronic acid, for example, and mixtures thereof, and it may be organically derived. Organically derived polysaccharides include *Alcaligenes* polysaccharides, and *Tremella fuciformis* polysaccharide (extracted from *Tremella fuciformis*), having glucuronic acid, mannose and xylose as constituent monosaccharides (for example, Tremoist TP, trade name of Nippon Seika Co., Ltd.).

The polysaccharide(s) content is preferably 0.01 mass % or greater, more preferably 0.05 mass % or greater and even more preferably 0.08 mass % or greater, and preferably no greater than 0.8 mass %, more preferably no greater than 0.5 mass % and even more preferably no greater than 0.3 mass %, based on the total mass of the liquid cosmetic. In other words, the polysaccharide(s) content may be from 0.01 to 0.8 mass %, from 0.01 to 0.5 mass %, from 0.01 to 0.3 mass %, from 0.05 to 0.8 mass %, from 0.05 to 0.5 mass %, from 0.05 to 0.3 mass %, from 0.08 to 0.8 mass %, from 0.08 to 0.5 mass % or preferably from 0.08 to 0.3 mass %, based on the total mass of the liquid cosmetic. This can further reduce damage to the agar shells of the capsules, or leakage of the oil component from the capsules.

The amphiphilic substance is a compound having both a hydrophilic structure and a hydrophobic (lipophilic) structure, an example of which is a polyoxyethylene structure as the hydrophilic structure and a hydrocarbon (e.g. long-chain alkyl group) structure as the hydrophobic structure. The amphiphilic substance is preferably nonionic, such amphiphilic substances including compounds obtained by addition polymerization of ethylene oxide to saturated and/or unsaturated fatty acid glycerides. A saturated and/or unsaturated fatty acid glyceride used in this case may consist of two or more types, and the saturated and/or unsaturated fatty acid glyceride may be partially or completely hydrogenated. The number of repeating oxyethylene structures from ethylene oxide formed by addition polymerization may be from 4 to 80, but is more preferably from 10 to 80, from 20 to 80, from 30 to 70 or preferably from 40 to 60. The amphiphilic substance performs the role of a solubilizer to dissolve components such as perfumes in the aqueous phase.

Amphiphilic Substance with an HLB Value of No Greater than 13

The liquid cosmetic of this embodiment also includes an amphiphilic substance with an HLB value of no greater than 13.

The Hydrophile-Lipophile Balance (HLB) value is calculated from the Inorganic-Organic Balance (IOB) value, obtained by an organic paradigm method (for example, Koda, Y., "Yuki Gainenzu—Kiso to Ouyou", pp. 11-17, Sankyo Publishing, 1984), and is expressed as follows.

$$HLB\ value = IOB\ value \times 10$$

When the amphiphilic substance is a mixture of two or more components, the HLB value is defined as the weighted average of the HLB value for each component.

The HLB value of the amphiphilic substance is 13 or smaller. If the HLB value is 13 or smaller it will be possible to prevent damage to the capsules while solubilizing the perfume. Moreover, if the HLB value is no greater than 13, then it will be possible to reduce turbidity of the oil component in the capsules when the liquid cosmetic is placed in a high temperature environment (for example, 50° C.), which occurs due to the amphiphilic substance infiltrating into the capsules together with water in the aqueous phase or components such as the low molecular polyol described below.

From this viewpoint the HLB value of the amphiphilic substance is no greater than 13, but it is preferably no greater than 12.7, more preferably no greater than 12.5 and even more preferably no greater than 12, and may be 7 or greater, 8 or greater, 9 or greater or 10 or greater. In other words, the HLB value of the amphiphilic substance may be from 7 to 13, from 7 to 12.7, from 7 to 12.5, from 7 to 12, from 8 to 13, from 8 to 12.7, from 8 to 12.5, from 8 to 12, from 9 to 13, from 9 to 12.7, from 9 to 12.5, from 9 to 12, from 10 to 13, from 10 to 12.7, from 10 to 12.5 or preferably from 10 to 12.

Amphiphilic substances with an HLB value of no greater than 13 include POE hydrogenated castor oils such as POE hydrogenated castor oil 50 (PEG-50 hydrogenated castor oil) and POE hydrogenated castor oil 40 (PEG-40 hydrogenated castor oil), POE castor oils such as POE castor oil 50 (PEG-50 castor oil), and POE (20) sorbitan tristearate (polysorbate 65) and POE (6) sorbitan monooleate (polysorbate 81). The amphiphilic substance is preferably POE hydrogenated castor oil 40.

The amphiphilic substance(s) content is preferably 0.05 mass % or greater, more preferably 0.1 mass % or greater and even more preferably 0.3 mass % or greater, based on the total mass of the liquid cosmetic. This can minimize damage to the outer shell of the capsule, and can further reduce production of turbidity with the passage of time. It can also increase the moisture retention effect on skin. The amphiphilic substance content is preferably no greater than 20 mass %, more preferably no greater than 10 mass % and even more preferably no greater than 5 mass %, based on the total mass of the liquid cosmetic.

In other words, the amphiphilic substance(s) content is preferably from 0.05 to 20 mass %, from 0.1 to 10 mass %, or more preferably from 0.3 to 5 mass % based on the total mass of the liquid cosmetic.

Perfume

The aqueous phase may additionally include a perfume. The perfume used may be one that is commonly employed in cosmetics, and it may be a natural perfume from a plant starting material such as a flower, fruit or herb, a natural perfume from a material derived from an animal such as a civet or beaver, a synthetic perfume based on an ester, ether, aldehyde, ketone, alcohol or hydrocarbon, and mixtures thereof. The perfume may also be a formulated perfume comprising any combination of those mentioned above.

The perfume(s) content is preferably no greater than 2.0 mass %, more preferably no greater than 1.5 mass % and even more preferably no greater than 1.0 mass %, based on the total mass of the liquid cosmetic. This will result in an excellent fragrance for the liquid cosmetic regardless of how small an amount is added. The perfume content is preferably 0.01 mass % or greater, more preferably 0.05 mass % or greater and even more preferably 0.08 mass % or greater, based on the total mass of the liquid cosmetic. In other words, the perfume(s) content is preferably from 0.01 to 2.0 mass %, from 0.05 to 1.5 mass %, or more preferably from 0.08 to 1 mass % based on the total mass of the liquid cosmetic.

Low Molecular Polyol

The aqueous phase may also contain a low molecular polyol. The low molecular polyol may be a glycol such as 1,3-propanediol, propylene glycol, butylene glycol, pentylene glycol, dipropylene glycol or polyethylene glycol, a glycerol such as glycerin, diglycerin or polyglycerin, a sugar alcohol such as sorbitol, and mixtures thereof. These low molecular polyols may be used alone or in combinations of two or more. A low molecular polyol, for the purpose of the present specification, is a polyol having a number-average molecular weight of no greater than 1000.

The low molecular polyol(s) content is preferably 3 mass % or greater, more preferably 5 mass % or greater and even more preferably 7 mass % or greater, based on the total mass of the liquid cosmetic. This will allow the moisturizing effect of the liquid cosmetic to be further increased, and will prevent decay of the liquid cosmetic so that it can be stored for prolonged periods. The low molecular polyol(s) content is also preferably no greater than 50 mass %, more preferably no greater than 40 mass % and even more preferably no greater than 30 mass %, based on the total mass of the liquid cosmetic. In other words, the low molecular polyol(s) content is preferably from 3 to 50 mass %, from 5 to 40 mass %, or more preferably from 7 to 30 mass % based on the total mass of the liquid cosmetic.

The liquid cosmetic of this embodiment may also contain appropriate amounts of mono-alcohols (excluding preservatives), preservatives (for example, aryloxyalkanols such as phenoxyethanol), pH regulators, electrolytes, emulsifiers, antioxidants, antifading agents stabilizers, and mixtures thereof.

An electrolyte can stabilize the liquid cosmetic while also exhibiting beautifying effects, including a moisturizing effect, or whitening and anti-inflammatory effects for skin, and examples of electrolytes include edetic acid, citric acid, lactic acid, glycolic acid, succinic acid, tartaric acid, malic acid, ascorbic acid, glycyrrhizinic acid, as well as their salts, and mixtures thereof. A single electrolyte may be used alone, or two or more may be used in combination.

The viscosity of the liquid cosmetic at 25° C. may be, for example, 50 mPa·s or higher, 60 mPa·s or higher or 80 mPa·s or higher, to no higher than 10,000 mPa·s, no higher than 5,000 mPa·s or no higher than 3,000 mPa·s. In other words, viscosity of the liquid cosmetic at 25° C. may be from 50 mPa·s to 10,000 mPa·s, in particular from 60 mPa·s to 5,000 mPa·s or preferably from 80 mPa·s to 3,000 mPa·s. The viscosity of the liquid cosmetic can be measured using a rotating viscometer (for example, Rheolab QC by Anton Paar, spindle: CC-27, rotational speed; 200 rpm, ST-22-4 V-40, rotational speed: 100 rpm, ST-24-2D/2 V/2 V-30, rotational speed: 50 rpm).

The liquid cosmetic of the embodiment having a viscosity in the aforementioned range has the capsules dispersed in the aqueous phase. That is to say, the liquid cosmetic does not have the capsules deposited or floating in the aqueous phase. The viscosity of the liquid cosmetic can be adjusted by varying the content of the (meth)acrylic polymer (s) and/or polysaccharide(s) disclosed above.

The liquid cosmetic is prepared by mixing water and an aryloxyalkanol as necessary, with addition of a (meth)acrylic polymer(s) and/or polysaccharide(s) to swell it. Mono-alcohols and other materials may then be added to and mixed with it as necessary. A low molecular polyol can be added and mixed with it before or after addition of a (meth)acrylic polymer(s) and/or polysaccharide(s).

The liquid cosmetics of each of the embodiments described above are particularly suitable for use as lotions (cosmetic water) and essences.

The present invention also relates to a cosmetic process for caring for and/or making-up keratinic materials, in particular providing a moisturizing, nourishing and emollient effect, comprising the application onto keratinic materials, in particular onto skin, of the liquid cosmetic as defined in the invention.

EXAMPLES

The invention will now be illustrated by examples, with the understanding that the invention is not meant to be limited to these examples. Unless contrary indication, the % are expressed in mass % also referred as % by weight of the total weight of the composition.

Examples 1 to 5, Comparative Examples 1 to 6

Liquid cosmetics containing capsules in aqueous phase were prepared with the compositions listed in Table 1. First, an aqueous phenoxyethanol solution (column "a") was heated to 80 to 85° C., after which a (meth)acrylic polymer (column "b") and/or a polysaccharide (column "c") were added to swell the (meth)acrylic polymer and/or polysaccharide. After then adding an aqueous solution of 2-amino-2-hydroxymethyl-1,3-propanediol (column "d"), a low molecular polyol (column "e"), an amphiphilic substance (column "f"), and a perfume (column "h") were mixed to solubilize the perfume. After that agar shell capsules encapsulating an oil component (column "h") were mixed to obtain a liquid cosmetic. The component contents (mass %) were as shown in Table 1.

<Stability Evaluation>
(1) One Month at 50° C.

Each cosmetic was filled into a transparent container and sealed with a cap, and then stored for 1 month at 50° C. After the storage period, each cosmetic was observed for the presence of any turbidity in the phase or capsules, or any leakage of the oil component from the capsules. Samples in which no turbidity of the phase or capsules and no leakage of oil components from the capsules was observed were evaluated as "A", those that exhibited turbidity were evaluated as "B", and those that had leakage of the oil component from the capsules were evaluated as "C". The results are shown in Table 1.

(2) One Month Under Cycle Conditions

Each cosmetic was filled into a transparent container and sealed with a cap, and then stored for one month under conditions with repeated temperature raising/lowering between −10° C. and 40° C. After the storage period, each cosmetic was observed for the presence of any turbidity in the phase or capsules, or any leakage of oil component from the capsules. Samples in which no turbidity of the phase or capsules and no leakage of oil components from the capsules was observed were evaluated as "A", those that exhibited turbidity were evaluated as "B", and those that had leakage of oil components were evaluated as "C". The results are shown in Table 1.

As the overall stability evaluation, samples that were stable without turbidity in the liquid cosmetic were evaluated as "Y", and samples with poor stability due to turbidity produced in the liquid cosmetic were evaluated as "N". The results are shown in Table 1.

TABLE 1

| Composition (mass %) | | | Example 1 | Example 2 | Example 3 | Example 4 | Example 5 | Comp. Example 1 | Comp. Example 2 | Comp. Example 3 | Comp. Example 4 | Comp. Example 5 | Comp. Example 6 |
|---|---|---|---|---|---|---|---|---|---|---|---|---|---|
| | A | Water | 44.68 | 44.68 | 44.68 | 24.68 | 24.68 | 44.68 | 44.68 | 44.68 | 44.68 | 24.68 | 24.68 |
| | | Phenoxyethanol | 0.4 | 0.4 | 0.4 | 0.4 | 0.4 | 0.4 | 0.4 | 0.4 | 0.4 | 0.4 | 0.4 |
| | B ((Meth)-acrylic polymer) | Acrylic acid-alkyl methacrylate copolymer (trade name: PEMULEN TR-2) | 0.1 | 0.1 | — | 0.1 | 0.1 | 0.1 | 0.1 | — | 0.05 | 0.1 | 0.1 |
| | C (Polysaccharide) | Sodium hyaluronate (trade name: BASHYAL POUDRE) | — | — | 0.1 | — | — | — | — | 0.1 | 0.05 | — | — |
| | D | Water | 4 | 4 | 4 | 4 | 4 | 4 | 4 | 4 | 4 | 4 | 4 |
| | | 2-Amino-2-hydroxymethyl-1,3-propanediol | 0.07 | 0.07 | 0.07 | 0.07 | 0.07 | 0.07 | 0.07 | 0.07 | 0.07 | 0.07 | 0.07 |
| | E | Glycerin | 10 | 10 | 10 | 20 | 20 | 10 | 10 | 10 | 10 | 20 | 20 |
| | | 1,3-Butylene glycol | 10 | 10 | 10 | 20 | 20 | 10 | 10 | 10 | 10 | 20 | 20 |
| | F (Amphiphilic substance) | PEG-40 hydrogenated castor oil (HLB value 12.0) (trade name: NIKKOL HCO-40) | 0.6 | — | 0.6 | 0.6 | — | — | — | — | — | — | — |
| | | PEG-50 hydrogenated castor oil (HLB value 13.0) (trade name: NIKKOL HCO-50) | — | 0.6 | — | — | 0.6 | — | — | — | — | — | — |

TABLE 1-continued

| | | Example 1 | Example 2 | Example 3 | Example 4 | Example 5 | Comp. Example 1 | Comp. Example 2 | Comp. Example 3 | Comp. Example 4 | Comp. Example 5 | Comp. Example 6 |
|---|---|---|---|---|---|---|---|---|---|---|---|---|
| | PEG-60 hydrogenated castor oil (HLB value 14.0) (trade name: NIKKOL HCO-60) | — | — | — | — | — | 0.6 | — | 0.6 | 0.6 | 0.6 | — |
| | PEG-60 hydrogenated castor oil (HLB value 14.0) (trade name: EUMULGIN CO 60) | — | — | — | — | — | — | 0.6 | — | — | — | 0.6 |
| G (perfume) | | 0.15 | 0.15 | 0.15 | 0.15 | 0.15 | 0.15 | 0.15 | 0.15 | 0.15 | 0.15 | 0.15 |
| H (Capsules) | Capsules [contents: glyceryl tri(caprylate/caprate)] | 30 | 30 | 30 | 30 | 30 | 30 | 30 | 30 | 30 | 30 | 30 |
| Stability Evaluation | 50° C. × 1 month | A | A | A | A | A | A | A | A | A | B | B |
| | −10 to 40° C. × 1 month | A | A | A | A | A | C | C | C | B | A | A |
| | Overall evaluation | Y | Y | Y | Y | Y | N | N | N | N | N | N |

For Examples 1 to 5, the stability was also evaluated after storage for one month at 4° C. The liquid cosmetics of Examples 1 to 5 were filled into transparent containers and sealed with a cap, and then stored for one month at 4° C. After the storage period, each cosmetic was observed for the presence of any turbidity in the phase or capsules, or any or leakage of oil component from the capsules. Samples in which no turbidity of the phase or capsules and no leakage of oil components from the capsules was observed were evaluated as "A", those that exhibited turbidity were evaluated as "B", and those that had leakage of the oil component were evaluated as "C". All of the liquid cosmetics of Examples 1 to 5 were evaluated as "A".

These results show that a liquid cosmetic according to the invention containing a capsule in an aqueous phase, wherein the capsule comprises agar shell encapsulating an oil component, and the aqueous phase comprises one thickener selected from the group consisting of (meth)acrylic polymers, polysaccharides and mixtures thereof, and an amphiphilic substance having an HLB value of no greater than 13, maintains high stability over time, in comparison to other comparative examples, so its original effect (moisturizing, emollient, nourishing effect) is maintained over long periods.

The invention claimed is:

1. A liquid cosmetic comprising a capsule in an aqueous phase, wherein the capsule comprises an agar shell encapsulating an oil component and the aqueous phase comprises one thickener selected from the group consisting of (meth)acrylic polymers, polysaccharides, and mixtures thereof, and an amphiphilic substance having an HLB value of no greater than 13 selected from among the group consisting of POE hydrogenated castor oil 50, POE hydrogenated castor oil 40, POE castor oil 50, and mixtures thereof, and wherein the (meth)acrylic polymers are selected from the group consisting of an alkyl (meth)acrylate copolymer, (meth)acrylic acid-alkyl (meth)acrylate copolymer or its salt, or a derivative or salt of a (meth)acrylic acid-alkyl (meth)acrylate copolymer, and their crosslinked forms, and mixtures thereof, and wherein the polysaccharides are selected in the group consisting of hyaluronic acid, sodium hyaluronate or acetylated hyaluronic acid, and organic derivatives, and mixtures thereof, wherein there is no leakage of oil components from capsules when the cosmetic composition is stored for one month at 4° C., or when the cosmetic composition is stored for one month under conditions with repeated temperature raising/lowering between −10° C. and 40° C.

2. The liquid cosmetic according to claim 1, wherein the oil component is selected in the group consisting of (1) an oil, (2) an oil soluble or dispersible component, and (3) a combination thereof.

3. The liquid cosmetic according to claim 2, wherein the oil (1) is selected from hydrocarbon oils, fat oils, waxes, hydrogenated oils, ester oils, fatty acids, silicone oils, fluorine-based oils, and mixtures thereof.

4. The liquid cosmetic according to claim 2, wherein the oil soluble or dispersible component (2) is selected from colorants, active ingredients, and mixtures thereof.

5. The liquid cosmetic according to claim 1, wherein the aqueous phase contains a perfume.

6. The liquid cosmetic according to claim 1, wherein the aqueous phase contains a low molecular polyol.

7. The liquid cosmetic according to claim 1, wherein the aqueous phase contains an aryloxyalkanol.

8. The liquid cosmetic according to claim 1, wherein capsules are dispersed in the aqueous phase.

9. A cosmetic process for caring for and/or making-up keratinic materials comprising the application onto keratinic materials of the liquid cosmetic as defined in claim 1.

10. The cosmetic process according to claim 9, wherein said caring for and/or making-up keratinic materials provides a moisturizing, nourishing, or emollient effect or mixtures thereof.

11. The cosmetic process according to claim 9, wherein said keratinic material is skin.

12. The liquid cosmetic according to claim 1, wherein the amphiphilic substance having an HLB value of no greater than 13 is POE hydrogenated castor oil 40.

\* \* \* \* \*